US00PP32971P2

(12) United States Plant Patent
Rouwette

(10) Patent No.: US PP32,971 P2
(45) Date of Patent: Apr. 13, 2021

(54) ***HYDRANGEA* PLANT NAMED 'GRYPAST05'**

(50) Latin Name: *Hydrangea paniculata*
Varietal Denomination: GRYPAST05

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 16/873,374

(22) Filed: Mar. 30, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A10H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea paniculata* plant named 'GRYPAST05' that is characterized by its inflorescences with sterile flower sepals that are creamy white in color and remain creamy white as they mature, its inflorescences with sterile flower sepals that are star-shaped, its compact plant habit, and its strong flower stems.

2 Drawing Sheets

Botanical classification: *Hydrangea paniculata.*
Varietal denomination: 'GRYPAST05'.

BACKGROUND OF THE INVENTION

The present invention relates to a new and distinct cultivar of *Hydrangea paniculata* and will be referred to hereafter by its cultivar name, 'GRYPAST05'. 'GRYPAST05' represents a new panicle *Hydrangea*, a perennial shrub grown for landscape use.

The new *Hydrangea* resulted from a controlled breeding program conducted by the Inventor in Valkenburg, The Netherlands. The Inventor made crosses in 2010 between unnamed and unpatented proprietary plants of *Hydrangea paniculata* in the Inventor's breeding program as both the female parent and male parent. The exact characteristics of the parents are unknown as seeds where pooled and sown from several crosses. 'GRYPAST05' was selected as a single unique plant in summer of 2013 from the resulting seedlings of the above crosses.

Asexual propagation of the new cultivar was first accomplished by stem cuttings by the Inventor in summer of 2013 in Valkenburg, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRYPAST05' as a unique cultivar of *Hydrangea paniculata.*

1. 'GRYPAST05' exhibits inflorescences with sterile flower sepals that are creamy-white in color and remain creamy-white as they mature.
2. 'GRYPAST05' exhibits inflorescences with sterile flower sepals that are star-shaped.
3. 'GRYPAST05' exhibits a compact plant habit.
4. 'GRYPAST05' exhibits strong flower stems.

'GRYPAST05' can be most closely compared to the *Hydrangea paniculata* cultivars 'Silver Dollar' (not patented) and 'Limelight' (U.S. Plant Pat. No. 12,874). Both are similar to 'GRYPAST05' in having inflorescences with sterile flower sepals that are white in color. 'Silver Dollar' differs from 'GRYPAST05' in having sterile flower sepals that are smaller in size and less star-shaped. 'Limelight' differs from 'GRYPAST05' in having smaller inflorescences with sterile flower sepals that are smaller in size, less star-shaped, and more green in color.

BRIEF DESCRIPTION OF THE DRAWINGS

The accompanying colored photographs illustrate the overall appearance and distinct characteristics of the new *Hydrangea*. The photographs were taken of a two-year-old plant of 'GRYPAST05' as grown outdoors in a 27-cm container in Boskoop, The Netherlands.

The photograph in FIG. 1 provides a side view of the plant habit of 'GRYPAST05' in bloom.

Figure 1:
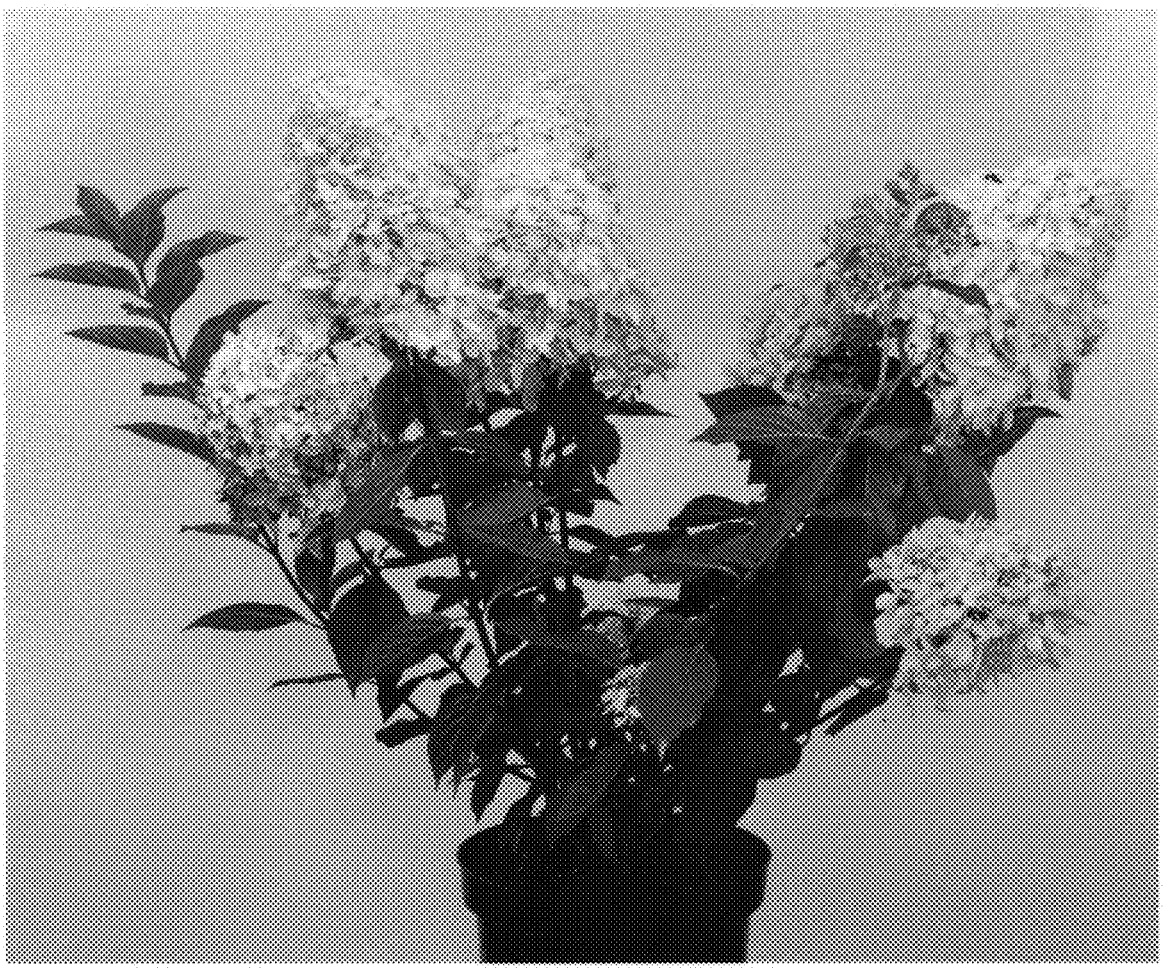
Figure 2:
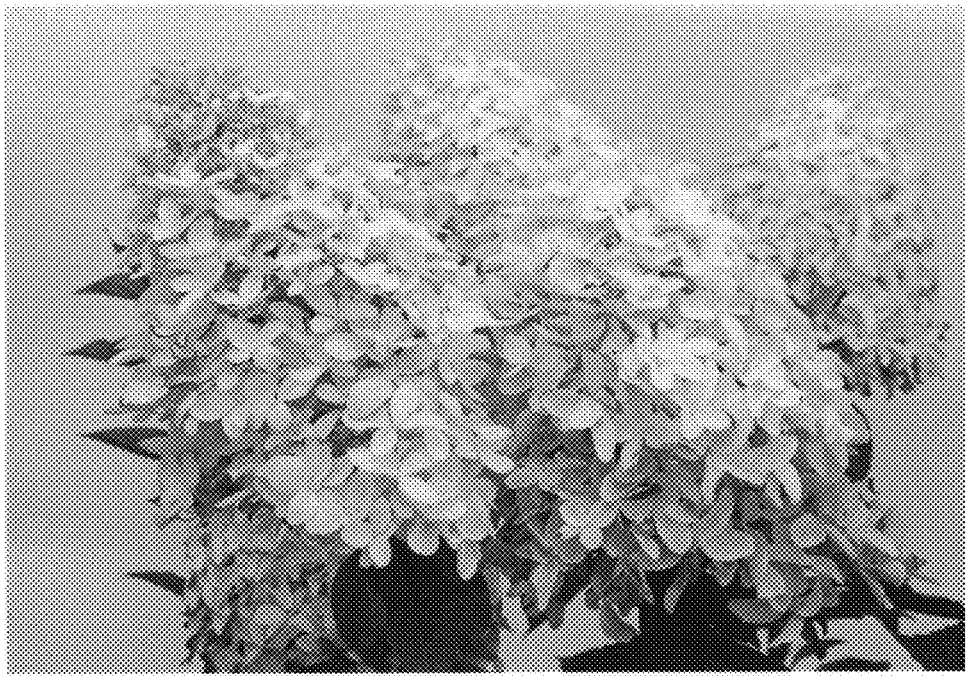

The photograph in FIG. 2 provides a close-up view of the inflorescences of 'GRYPAST05'.

Figure 3:
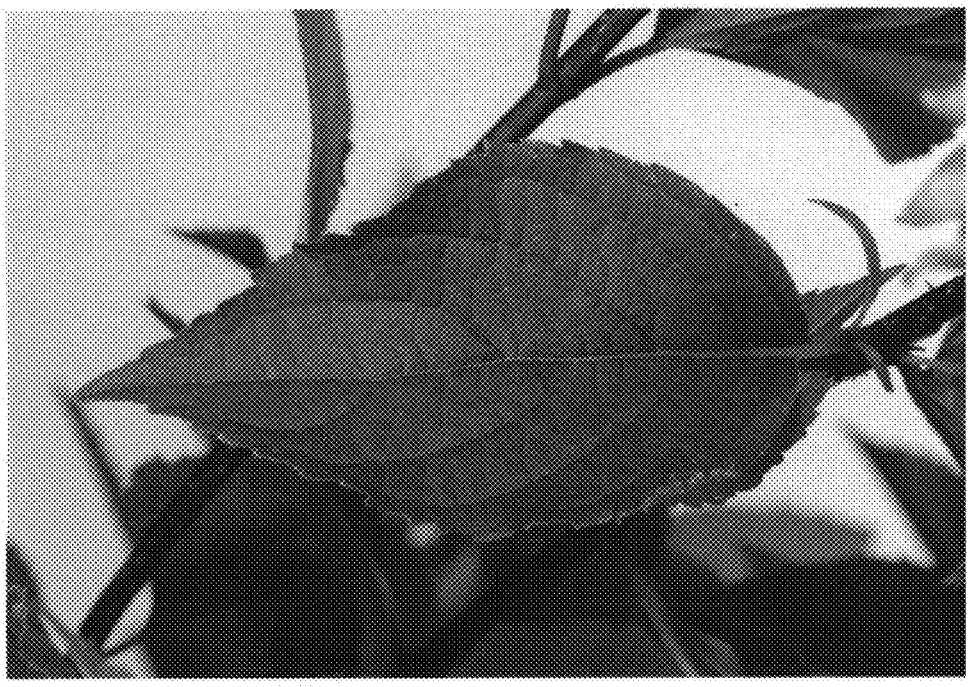

The photograph in FIG. 3 provides a close-up view of a leaf of 'GRYPAST05'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'GRYPAST05' as grown outdoors in 27-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to September in The Netherlands.

*Plant type*.—Upright, slightly spreading, and compact.

*Height and spread*.—Reaches 130 cm in height and 80 cm in spread as a mature plant in the landscape.

*Hardiness*.—At least in U.S.D.A. Zones 4 to 9.

*Diseases and pests*.—No susceptibility and resistance to diseases or pests has been observed.

*Root description*.—Fine, fibrous and dense, NN155A and 164A in color.

*Propagation*.—Stem cuttings.

*Root development*.—6 to 8 weeks for root initiation with a finished plant produced in about 12 months from a rooted cutting in a P9 container.

*Growth rate and vigor*.—Moderate to high.

Stem description:

*Stem shape*.—Rounded.

*Stem strength*.—Strong.

*Stem color*.—Young; 145A to 145B, mature; N199B, old bark; 197B to 197C.

*Stem size*.—Average of 46.6 cm in length (excluding inflorescence) and 7 mm in diameter.

*Stem surface*.—Young stems are matte and densely covered with stiff hairs, average of 0.5 mm in length and match surface color, mature stems are matte and moderately covered with lenticels that are an average of 1.5 mm in length and 0.75 mm in diameter, 164D in color, fasciation absent.

*Stem aspect*.—Upright, average of 55° to soil level, varying between 40° and 90°.

*Internode length*.—An average of 6 cm.

*Branching*.—Freely branching with an average of 16 lateral branches.

Foliage description:

*Leaf shape*.—Elliptic to ovate.

*Leaf arrangement*.—Opposite or in whorls of three.

*Leaf division*.—Simple.

*Leaf base*.—Attenuate.

*Leaf apex*.—Narrow apiculate.

*Leaf margins*.—Serrate, lobing absent.

*Leaf venation*.—Pinnate, color; upper surface 148A, lower surface 146D.

*Leaf size*.—An average of 11.3 cm in length and 6 cm in width.

*Leaf attachment*.—Petiolate.

*Leaf number*.—An average of 16 per lateral stem.

*Leaf surface*.—Both surfaces; smooth and very slightly rugose, upper surface moderately covered with short strigose hairs, lower surface main veins and secondary veins moderately covered with short strigose hairs, an average of 0.4 mm in length and 157A in color.

*Leaf color*.—Young upper surface; 144A, young lower surface 144B, mature upper surface; NN137C, mature lower surface; 147B, non-variegated.

*Petioles*.—An average of 1.7 cm in length and 2.5 mm in diameter, upper surface color 144B, proximal end 146A to 146B, lower surface color 144B, proximal end 146B, both surfaces matte and sparsely covered with very short hairs an average of 0.3 mm in length and too small to measure color.

Inflorescence description:

*Inflorescence type*.—Terminal conical panicle, comprised of sterile flowers above inconspicuous fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 22.7 cm in height and 18.3 cm in diameter.

*Flower number*.—An average of 450 sterile flowers and 200 fertile flowers per panicle.

*Flower fragrance*.—Moderate, sweet and pleasant.

*Flower aspect*.—Sterile flowers; held upright to outward and slightly drooping, fertile flowers; held upright from peduncle.

*Flower size*.—Sterile flowers; up to 4.2 cm in diameter and 1.2 cm in depth, fertile flowers; an average of 1.3 cm in diameter and 7 mm in depth.

*Flower type*.—Sterile flowers single, rotate, fertile flowers rotate, dropped when mature.

*Flower buds*.—Sterile flowers; an average of 5 mm in length and 1.3 cm in diameter, broadly cup-shaped, 145C and 145D in color, fertile flowers; an average of 3.5 mm in length, 3 mm in diameter, obovate in shape, color; 157D, immature calyx 193A to 193B.

*Petals*.—Sterile flowers; 5 (occasionally 4), ovate to concave in shape, acute apex, entire margins, cuneate base, up to 3.5 mm in length and 2 mm in width, upper surface glabrous and slightly glossy, lower surface glabrous and matte, color when opening and fully open upper and lower surface NN155D, fertile flowers; 5, rotate in shape, ovate to concave in shape, acute apex, cuneate base, entire margins, average of 4 mm in length and 2.5 mm in width, both surfaces glabrous, upper surface slightly glossy, lower surface matte, color; when opening and fully open upper and lower surface NN155D, petals drop at maturity.

*Peduncles*.—Primary peduncles; strong, flattened oval in shape, an average of 3 cm in length and 2 mm in width. secondary peduncles 2 cm in length and 2 mm in width, 157A in color, surface is matte and moderately covered with thin pubescence an average of 0.3 mm in length and 145D in color.

*Pedicels*.—Sterile flowers; moderate strength, an average of 2.6 cm in length and 1 mm in width, 157A in color, surface is pubescent, held at a 50° angle, 145D in color, surface is matte and moderately covered with thin pubescence an average of 0.3 mm in length and 157D in color, fertile flowers; moderate strength, an average of 2 mm in length, 0.5 mm in diameter, held at a 30° angle, 145D in color, surface is matte and densely covered with thin pubescence an average of 0.3 mm in length and 145D in color.

*Sepals*.—Sterile flowers; 4 (occasionally 5), rotate, elliptic to obovate and ovate, slightly concave and carinate in shape, obtuse apex, obtuse to short attenuate base, entire margins, up to 2.4 cm in length and 1.8 cm in width, both surfaces; glabrous and matte, color; upper and lower surface when opening 155C, upper and lower surface when fully open 155A, maturing flower color; upper surface changing to 145B, lower surface changing to 145B and 145C, fertile flowers; 5, rotate, broadly deltoid in shape, broad acuminate apex, broad cuneate base, entire margins, 1 mm in length, 1.5 mm in width, both surfaces glabrous and matte, color; when opening upper surface 193B, when opening lower surface 193A to 193B, when fully open upper surface and lower surface 145C.

*Bracts*.—1 present on each pedicel, narrow elliptic in shape, acute apex, acute base, entire margins, 1.2 cm in length, 4 mm in width, both surfaces 145B in color.

Reproductive organs:

*Gynoecium*.—Sterile flowers; 1 pistil, an average of 1 mm in length, stigma; pointed in shape and 157D in color, style; 0.5 mm in length, 150D in color, ovary; 150D in color, fertile flowers; 3 pistils, an average of 2 mm in length, stigma; club-shaped and 157D in color, style; 1 mm in length, 150D in color, ovary is 150D in color.

*Androecium*.—Sterile flowers; stamens; average of 8, filaments; 3 mm in length and NN155D in color, anthers; broad oblong in shape, 0.5 mm in length, 155D in color, pollen; moderate in quantity, 156C in color, fertile flowers; stamens; average of 10, filaments; 6 mm in length, NN155D in color, anthers; broad oblong in shape, 0.5 mm in length, 155D in color, pollen; moderate quantity, 156C in color.

*Fruit and seed*.—None observed to date.

It is claimed:

1. A new and distinct cultivar of *Hydrangea* plant named 'GRYPAST05' substantially as herein illustrated and described.

* * * * *